United States Patent
Deguchi et al.

(10) Patent No.: US 7,566,884 B2
(45) Date of Patent: Jul. 28, 2009

(54) SPECIMEN HOLDER FOR ELECTRON MICROSCOPE

(75) Inventors: Shunji Deguchi, Tokyo (JP); Yukihito Kondoh, Tokyo (JP)

(73) Assignee: Jeol Ltd., Tokyo (JP)

( * ) Notice: Subject to any disclaimer, the term of this patent is extended or adjusted under 35 U.S.C. 154(b) by 424 days.

(21) Appl. No.: 11/440,695

(22) Filed: May 25, 2006

(65) Prior Publication Data

US 2006/0289784 A1 Dec. 28, 2006

(30) Foreign Application Priority Data

May 30, 2005 (JP) ............................. 2005-157124

(51) Int. Cl.
*G21K 5/10* (2006.01)
(52) U.S. Cl. .............................. 250/442.11; 250/441.11; 250/310
(58) Field of Classification Search ............. 250/442.11
See application file for complete search history.

(56) References Cited

U.S. PATENT DOCUMENTS 3,896,314 A * 7/1975 Nukui et al. ........... 250/442.11
6,967,335 B1 * 11/2005 Dyer et al. ............. 250/442.11

FOREIGN PATENT DOCUMENTS

JP 5-69660 9/1993
JP 2003-35682 2/2003

* cited by examiner

*Primary Examiner*—David A. Vanore
*Assistant Examiner*—Phillip A. Johnston
(74) *Attorney, Agent, or Firm*—The Webb Law Firm (57) ABSTRACT

A specimen holder has two levers on which probes for current measurement are carried. The levers are in contact with a spherical body, the spherical body acting as a pivotal point. When the levers are pushed by micrometer heads, the probes move in the X-direction. When the levers are pulled, the probes are pushed back by springs and move in the −X-direction. When the first lever is pushed by a further micrometer head, the first probe rotates about the spherical body and thus moves in the Y-direction. When the first lever is pulled, the first probe is pushed back by the first spring and moves in the −Y-direction. The second probe is moved along the Y-axis by similarly manipulating a further micrometer head. The two probes can be moved along the Z-axis by similarly manipulating other micrometer heads.

8 Claims, 6 Drawing Sheets

SPECIMEN HOLDER FOR ELECTRON MICROSCOPE

BACKGROUND OF THE INVENTION

1. Field of the Invention

The present invention relates to a specimen holder for holding a specimen in the electron beam path within a transmission electron microscope (TEM) and, more particularly, to a specimen holder which permits imaging of the specimen while supplying electrical current to the specimen or taking an electrical signal from it.

2. Description of Related Art

Since a TEM enables high spatial-resolution imaging and analysis, the TEM is an instrument indispensable for evaluation of materials in the submicroscopic domain. The TEM makes it possible to perform high spatial-resolution imaging. In addition, variations in the specimen can be observed while heating, cooling, or stretching the specimen or applying a voltage to the specimen. In this way, a richer amount of knowledge can be derived from the specimen. Consequently, TEMs are used in many material fields.

For example, in a specimen used in the semiconductor microelectronics field, the resistance value of the specimen is measured while electrically energizing the specimen or taking an electrical signal from the specimen before and after the energization. Thus, information about the characteristics of the material of the specimen can be obtained. However, since the specimen observed on the TEM is placed in the narrow gap between the objective lens polepieces, limitations are imposed on the shape and functions of the specimen holder. Techniques regarding specimen holders permitting such measurements and observations are disclosed in Japanese Patent Laid-Open No. 2003-35682 and Japanese Utility-Model Laid-Open No. H5-69660.

Japanese Patent Laid-Open No. 2003-35682 discloses a technique for measuring the electrical characteristics of the inside of an LSI having a design rule of about 0.1 μm using a focused ion beam (FIB) machine and a TEM. In this technique, a pair of very thin conductors is moved into a desired measurement site on the specimen by a manipulateor. The conductors are fixed to the measurement site by FIB processing. Then, the specimen holder is removed from the FIB machine and attached to the TEM or other apparatus. Then, measurements and observations can be carried out. In this method, however, a probe for measurement must be fixed to a desired measurement site by the manipulator and FIB machine before the specimen is placed on the TEM. Therefore, even if a desired measurement site is found from the results of high-magnification TEM image observation, the site cannot be measured.

Japanese Utility-Model Laid-Open No. H5-69660 discloses a specimen holder used for measurement of electrical resistance. This holder is employed in a four-terminal method in electron microscopy. The holder has two opposite specimen supports across which a specimen is placed. A lead wire for applying a voltage to the specimen is previously connected with the opposite specimen supports. Two terminals for measuring the voltage drop across the specimen are connected with the specimen via the two specimen supports. In this method involving bringing the two terminals into contact with the specimen, however, a quite thin lead wire is directly soldered to ends of the specimen or electrical conductivity is obtained by wire having resilience. Consequently, it is impossible to make measurement at a microscopic measurement site selected on the specimen.

SUMMARY OF THE INVENTION

It is an object of the present invention to provide a specimen holder which solves the foregoing problems and which permits measurement of the electrical characteristics (such as electrical conductivity) of a quite small part of a specimen of interest from results of a high-magnification TEM image observation.

A first embodiment of the present invention, which is free of the foregoing problems, provides a specimen holder having a holder outer cylinder that is movably supported by a specimen holder installation member extending through the electron optical column of an electron microscope. The holder outer cylinder can move in the direction of the axis of the holder which extends through the electron optical column and intersects the electron beam path. The specimen holder has a specimen support member supported to the front end of the holder outer cylinder, specimen holding means that electrically insulates the specimen from the specimen support member, and a probe position fine adjustment mechanism whose position can be adjusted along three orthogonal axes including the axis of the holder. The specimen support member has an opening permitting passage of an electron beam. The specimen holding means holds the specimen in such a way that the holding means plugs a part of the opening. The probe position fine adjustment mechanism brings at least two probes for electrical current measurement into desired locations on the specimen.

A second embodiment of the present invention is based on the first embodiment described above and further characterized in that the probe position fine adjustment mechanism has a lever carrying the probe on its front-end portion while electrically insulated from the probe, a spherical body which can move the lever in the direction of the axis of the holder and which acts as a pivotal point permitting movement of the front end of the probe by rotation in two axial directions perpendicular to the axis of the holder, a support member for supporting the lever to the holder outer cylinder, a translational motion mechanism mounted at the end of the lever located on the opposite side of the end of the lever carrying the probe with the spherical body interposed between them and acting to move the lever in the three axial directions including the direction of the axis of the holder, and a resilient body for pushing the lever back to a position located opposite to the translational motion mechanism with the lever interposed between them.

A third embodiment of the present invention is based on the first or second embodiment described above and further characterized in that the probe position fine adjustment mechanism has a spherical body fixed in the direction of the axis of the holder, two levers holding the spherical body therebetween, and resilient bodies each located between the holder outer cylinder and a respective one of the levers. Sides of the levers abutting against the spherical body are provided with V-grooves. The resilient body brings the spherical body into intimate contact with the V-grooves. Relative movement between the spherical body and each lever moves the probe in the direction of the axis of the holder. The probe is moved along the two axes perpendicular to the direction of the axis of the holder by rotation of the lever about the spherical body located between the two ends of the lever. This rotation is produced by translational motion of the end of the lever that is on the opposite side of the end of the lever carrying the probe, the translation motion being made along the two axes perpendicular to the direction of the axis of the holder. During this rotation, the V-grooves in the lever against which the spherical body abuts are used as sliding portions.

A fourth embodiment of the present invention is based on the first or second embodiment and further characterized in that the probe position fine adjustment mechanism has two levers and a spherical body support member fixedly mounted to the holder outer cylinder. The levers are fitted in throughholes in two spherical bodies and fixed to prevent them from moving relative to the spherical bodies. The spherical body support member has two cylindrical holes in which the two spherical bodies can move in the direction of the axis of the holder. Movement of the probe in the direction of the axis of the holder is made by movement of the spherical bodies relative to the inner walls of the cylindrical holes. Movement of the probe along the two axes perpendicular to the direction of the axis of the holder is made by rotation of the probe along the spherical body which are interposed between the two ends of the lever. The rotation is produced by translational motion of the end of the lever opposite to the end of the lever carrying the probe thereon along the two axes perpendicular to the direction of the axis of the holder. During this rotation, the contact portions between respective ones of the spherical bodies and the spherical body support member act as sliding portions.

A fifth embodiment of the present invention is based on the first or second embodiment described above and further characterized in that the probe position fine adjustment mechanism has two spherical bodies, two levers, a spherical body support member fixed to the holder outer cylinder, and a spherical body-pushing member pushing the spherical bodies against the spherical body support member. Each of the spherical bodies is provided with a hole extending through it along the axis of the holder. The levers are fitted in the through-holes in the spherical bodies and can move relative to the spherical bodies in the direction of the axis of the holder. The spherical body support member has abutment portions which abut against the spherical bodies. Each abutment portion has a conical seat. The spherical body-pushing member pushes the spherical bodies into intimate contact with the conical seats of the spherical body support member.

The probe is moved in the direction of the axis of the holder by moving the levers relative to the through-holes in the spherical bodies. The probe is moved along two axes perpendicular to the direction of the axis of the holder by rotation of the probe about the spherical bodies. The rotation is produced by translational motion of the end of the lever located on the opposite side of the end of the lever carrying the probe thereon with the spherical bodies interposed between them, the translational motion being made along two axes perpendicular to the direction of the axis of the holder. During this rotation, the conical seats of the spherical body support member abutting against the spherical bodies and the spherical body-pushing member act as sliding portions.

A sixth embodiment of the present invention is based on any one of the first through fifth embodiments and further characterized in that the probe position fine adjustment mechanism has piezoelectric devices each incorporated between the translational motion mechanism and a respective one of the levers.

A seventh embodiment of the present invention is based on any one of the first through sixth embodiments and further characterized in that the probe position fine adjustment mechanism incorporates a motor for driving the translational motion mechanism.

An eighth embodiment of the present invention is based on any one of the first through seventh embodiments and further characterized in that there is further provided an electrode which is mounted to the specimen support member but electrically insulated from the support member. The electrode has a terminal making contact with the specimen.

A ninth embodiment of the present invention is based on any one of the first through eighth embodiments and further characterized in that there are further provided at least two specimen-holding members in contact with the specimen at different positions to hold the specimen to the specimen support member. The specimen-holding members can be used as electrodes electrically insulated from the specimen support member.

With the specimen holder according to the first embodiment described above, the electrical conductivity between desired two points on the specimen can be measured either during TEM imaging or before and after TEM imaging.

With the specimen holder according to the second embodiment described above, the probe can be brought into contact with the specimen at a desired position by moving the probe in three dimensions by the use of a combination of translational and rotational motions.

With the specimen holder according to the third embodiment described above, the probe is moved in three dimensions by combining translational and rotational motions. The probe can be brought into contact with the specimen at a desired location.

With the specimen holder according to the fourth embodiment described above, the probe can be brought into contact with the probe at a desired location by moving the probe in three dimensions by the use of a combination of translational and rotational motions.

With the specimen holder according to the fifth embodiment described above, the probe can be brought into contact with the specimen at a desired location by moving the probe in three dimensions by the use of a combination of translational and rotational motions.

With the specimen holder according to the sixth embodiment described above, movement of the probe can be controlled more finely. A desired measurement site can be selected while observing an image with higher resolution.

With the specimen holder according to the seventh embodiment described above, it is not necessary for the human operator to touch the micrometer head directly with his hand. Therefore, the observed image can be prevented from being affected by mechanical vibrations. This improves the manipulability and enables remote manipulation.

With the specimen holder according to the eighth embodiment described above, electrical characteristics can be measured by a three-terminal method during TEM imaging or before and after TEM imaging using two probes and a terminal that is brought into contact with the specimen at a fixed location. The probes permit selection of measurement sites.

With the specimen holder according to the ninth embodiment described above, electrical characteristics can be measured by a four-terminal method during TEM imaging or before and after TEM imaging using two probes and two terminals which are brought into contact with the specimen at fixed locations. The two probes permit selection of measurement sites.

Other objects and features of the invention will appear in the course of the description thereof, which follows.

DESCRIPTION OF THE PREFERRED EMBODIMENTS

Embodiments of the present invention are hereinafter described with reference with the accompanying drawings. In the following description, the invention is applied to an electron microscope but the invention is not limited thereto. For example, the invention can also be applied to a general charged-particle beam apparatus having a side entry structure. Note that components having identical or similar functions are indicated by the same numerals in the various figures and will not be described repeatedly.

To facilitate understanding the following description, mutually perpendicular coordinate axes X-, Y-, and Z-axes are defined and denoted in the figures. The symbol circle ○ with a dot "●" in its center indicates an arrow directed from the reverse side to the front side of the paper. The symbol circle ○ with a cross "x" in its center indicates an arrow directed from the front side to the reverse side of the paper. In the figures, the axis of the holder extending through the electron optical column of an electron microscope so as to intersect the electron beam path lies on the X-axis. A horizontal direction perpendicular to the axis of the holder is taken as the Y-axis. A direction parallel to the axis of the irradiating electron beam is taken as the Z-axis.

Figure 1:
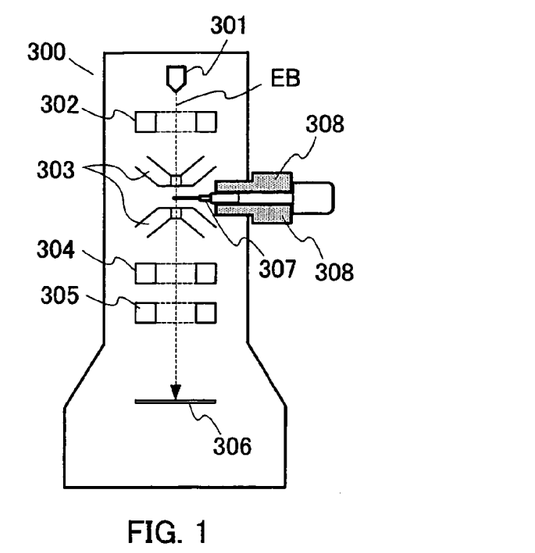
FIG. 1 is a side elevation of an electron microscope adapted to be used with a side entry specimen holder and in which the specimen holder has been installed.

FIG. 1 shows the state in which a specimen holder 307 has been mounted in a transmission electron microscope. In the state of FIG. 1, the inside of the electron optical column 300 is maintained as a vacuum. The microscope has an electron gun 301 emitting an electron beam EB which is focused onto a specimen by a system of condenser lenses 302. The specimen to be observed is placed on a front-end portion of the specimen holder 307 which is loaded on a specimen stage 308. The holder 307 is supported by a specimen holder installation member. The front-end portion of the holder 307 is inserted in the gap between objective lens polepieces 303, and the observed specimen is held in the electron beam path. The specimen stage 308 is equipped with a specimen-moving mechanism and a tilting mechanism (none of which are shown). The position of the electron beam EB on the specimen can be varied while illuminating the specimen with the electron beam. The electron beam transmitted through the specimen is passed through an intermediate lens system 304 and a projector lens system 305 and forms a visible image on a fluorescent screen 306. If necessary, the image is recorded using film, CCD camera, or other means (not shown).

Embodiment 1

Figures 2A, 2B, 2C, 2D:
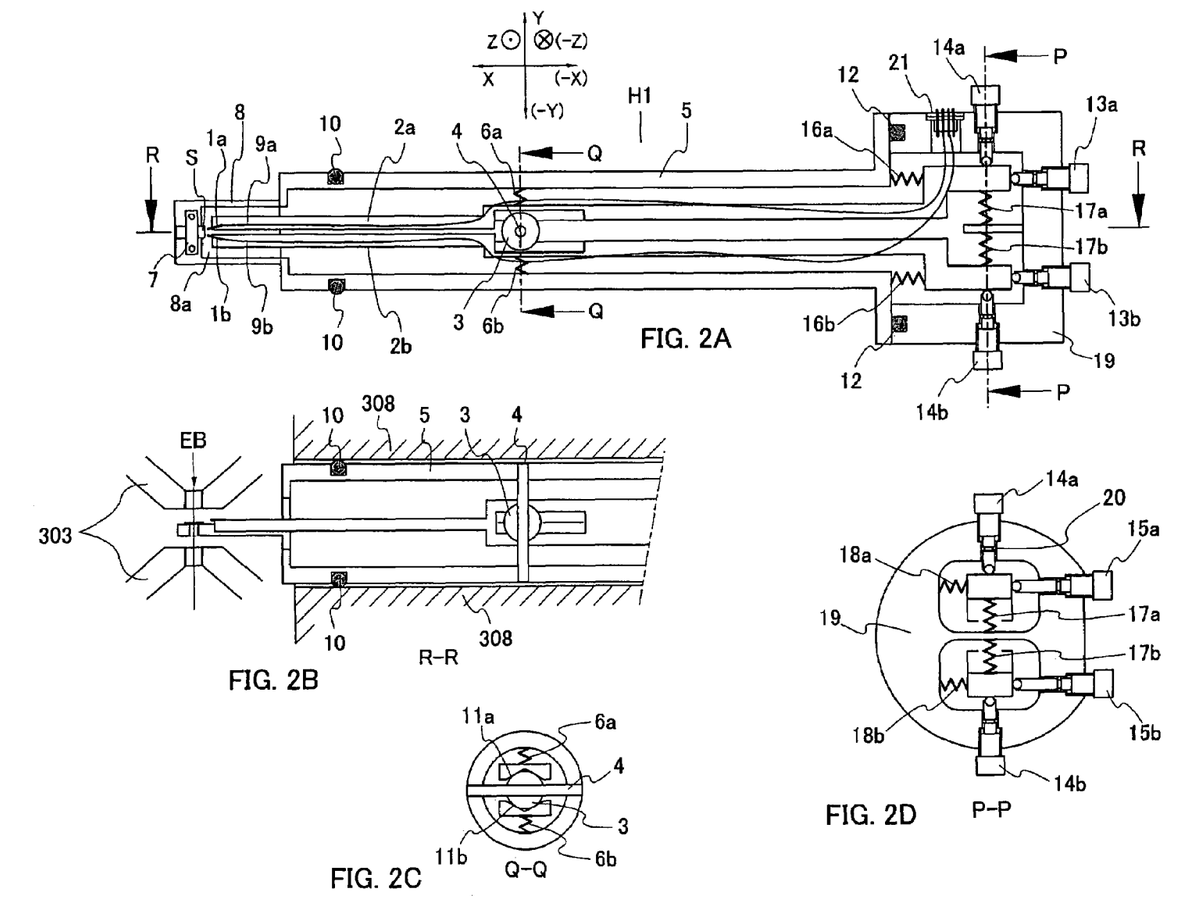
FIGS. 2A-2D show a specimen holder according to an embodiment of the present invention.
Figure 6A:
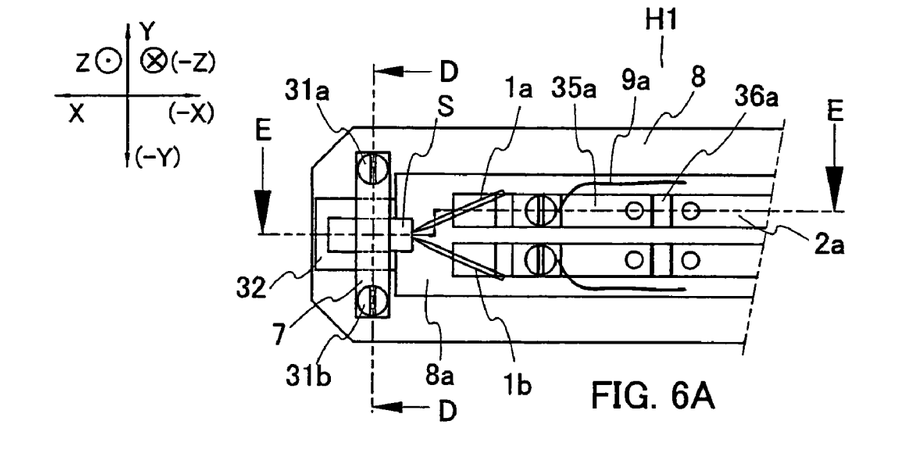
FIGS. 6A-6C show a front-end portion of a specimen holder according to the present invention in enlarged form.
Figure 6B:
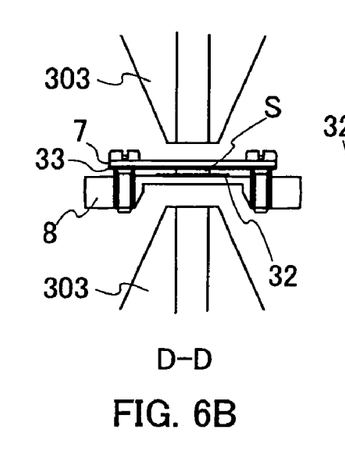
Figure 6C:
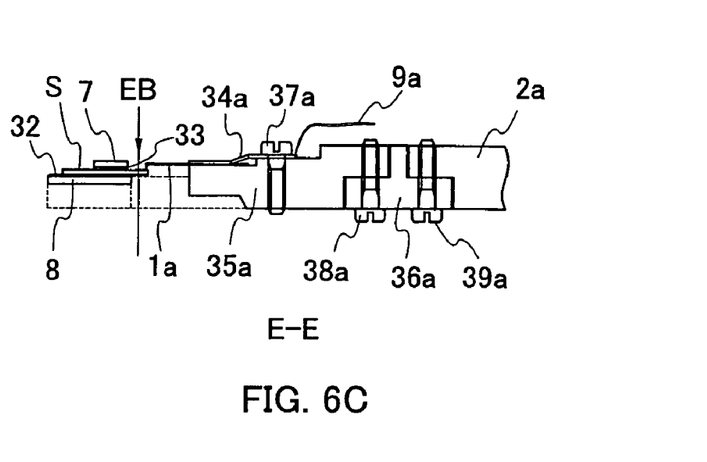

FIGS. 2A-2D show a specimen holder according to an embodiment of the present invention. FIG. 2A is a plan view of the specimen holder H1 as viewed from the side of the electron gun 301. FIG. 2B is a fragmentary cross section taken on line R-R of FIG. 2A. FIGS. 2C and 2D are cross-sectional views taken on lines Q-Q and P-P, respectively, of FIG. 2A. FIGS. 6A, 6B, and 6C show the front-end portion of the specimen holder H1 in enlarged form. FIG. 6A is a plan view of the front-end portion as viewed from the electron gun side. FIGS. 6B and 6C are cross-sectional views taken on lines D-D and E-E, respectively, of FIG. 6A. As shown in FIG. 6B, a specimen S is inserted in the narrow gap between the top and bottom polepieces 303 of the objective lens and tilted. For this purpose, the front end of the specimen holder H1 is made quite thin. To facilitate understanding the structure, the vertical dimension of the holder is shown to be exaggerated about twice compared with the actual dimension.

Referring to FIGS. 6A-6C, the specimen S is placed on an insulator 32 which, in turn, is disposed on a specimen support member 8. The specimen S is supported by a specimen holding member 7 via another insulator 33 and thus is electrically insulated. Screws 31a and 31b which fix the specimen holding member 7 are electrically insulated from the specimen support member 8 by a further insulator (not shown). The observed portion of the specimen S is supported to overhang the opening 8a. The electron beam EB can be transmitted through the specimen S. The relation of the thickness of the specimen support member 8 to the thicknesses of the specimen S, specimen holding member 7, and insulators 32, 33 is different from the actual value; the vertical positional relationship is schematically shown for clarity.

In FIGS. 6A-6C, a probe 1a for current measurement has a sharp front-end portion. A probe support member 35a is supported to the front end of the lever 2a. The probe 1a is supported to the probe support member 35a by a probe holding member 34a and a screw 37a. The probe holding member 34a and an electrical wire 9a are electrically connected together. The wire 9a is connected with an airtight terminal 21, so that an electrical signal can be taken out of the vacuum environment. The probe support member 35a and lever 2a are electrically insulated by an insulator member 36a. The insulator member 36a is mounted to the probe support member 35a and to the lever 2a by screws 38a and 39a.

Referring to FIGS. 2A-2D, when the levers 2a and 2b are driven, they rotate about a spherical body 3. A shaft 4 for fixing the spherical body 3 is mounted to the holder outer cylinder 5 and extends through the spherical body 3. V-grooves 11a and 11b are formed on the sides of the levers 2a and 2b on which the levers 2a and 2b contact the spherical body 3. The levers can translate along the X-axis and rotate along the Y- and Z-axes. Springs 6a and 6b are mounted to bring the sliding portions of the spherical body 3 into intimate contact with the V-grooves 11a and 11b in the levers 2a and 2b.

The electrical wires 9a and 9b connected with the probes 1a and 1b, respectively, are connected with the airtight terminal 21, so that an electrical signal can be taken out of the vacuum environment. An O-ring 10 is disposed between the holder outer cylinder 5 and the specimen stage 308 to maintain the vacuum in the electron optical column 300 of FIG. 1. Another O-ring 12 is disposed between the holder outer cylinder 5 and a translational motion mechanism support member 19 to maintain the vacuum inside the specimen holder H1. In the example of FIGS. 2A to 2D, micrometer heads are used as the translational motion mechanism. As shown in FIG. 2D, an O-ring 20 is disposed between each micrometer head and the translational motion mechanism support member 19 to maintain the vacuum inside the specimen holder H1. Only the O-ring for a micrometer head 14a is representatively indicated by reference numeral 20. Similar O-rings are similarly disposed for the other micrometer heads.

The probes 1a and 1b are moved in the X-direction by pushing the levers 2a and 2b in the X-direction using the micrometer heads 13a and 13b. Since springs 16a and 16b are mounted in positions opposite to the micrometer heads 13a and 13b, respectively, to push back the levers, the probes 1a and 1b can be moved in the –X-direction by manipulating the micrometer heads in the direction to pull them. At this time, the V-grooves in the levers 2a and 2b with which the spherical body 3 is in contact act as sliding portions.

The probes 1a and 1b are moved along the Y- or Z-axis by pushing or pulling the –X-direction ends of the levers 2a and 2b along the Y- or Z-axis by means of the micrometer heads 14a, 14b, 15a, and 15b. For example, the probe 1a is moved in the Y-direction as follows. First, the –X-direction end of the lever 2a is pushed in the –Y-direction by means of the micrometer head 14a. At this time, the probe 1a rotates about the spherical body 3 in the Y-direction. During this rotation, the portion of the spherical body 3 that bears against the V-groove 11a in the lever 2a acts as a sliding portion. A spring 17a is mounted in a position opposite to the micrometer head 14a to push back the lever 2a. Therefore, the probe 1a can be rotated in the –Y-direction if the micrometer head 14a is manipulated in the direction to pull it. Manipulations of the micrometer head 14b and manipulations of the micrometer heads 15a, 15b for moving the probes 1a and 1b along the Z-axis are performed on the same principle as the aforementioned manipulation of the micrometer head 14a and so their description is omitted.

That is, the probe position fine adjustment mechanism of the specimen holder H1 is made up of the levers 2a, 2b, spherical body 3, shaft 4 for fixing the spherical body, micrometer heads 13a, 13b, 14a, 14b, 15a, 15b, and springs 6a, 6b, 16a, 16b, 17a, 17b, 18a, 18b.

A manipulation for moving the sharp front end of each of the probes 1a and 1b into a desired current measurement site on the specimen can be performed while observing the electron microscope image. The minimum distance between two points across which an electrical current can be measured depends on the thickness of the front end of the probe.

Embodiment 2

Figure 3A:
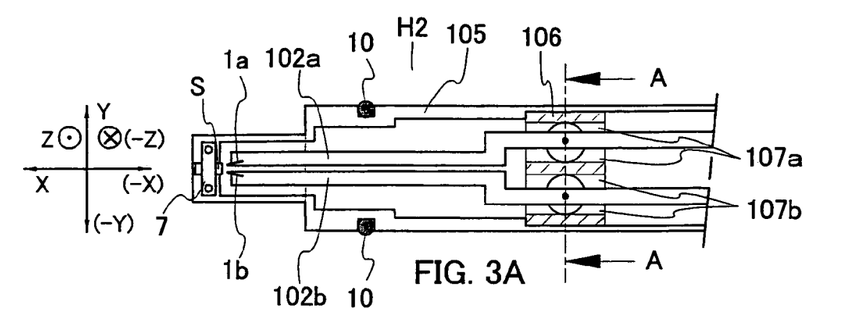
FIGS. 3A and 3B show another example of pivotal structure for moving a probe for current measurement in three dimensions.
Figure 3B:
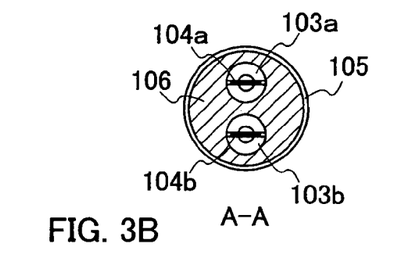

Another example of the structure of the pivotal point for moving the probes 1a and 1b in three dimensions is next described by referring to FIGS. 3A-3B. FIG. 3A is a plan view of the specimen holder H2 as viewed from a side of the electron gun 301. The right half (on the negative side of the X-axis) of the specimen holder H2 is identical in structure and function with the specimen holder H1 of FIG. 2A and so is not shown. FIG. 3B is a cross-sectional view taken on line A-A of FIG. 3A. The electrical wires 9a and 9b connected with the probes 1a and 1b are not shown such that the figures can be read more easily.

Levers 102a and 102b are fixed to spherical bodies 103a and 103b, respectively, by means of fixing pins 104a and 104b, respectively. The spherical bodies 103a and 103b act as pivotal points when motion is induced. A spherical body support member 106 fixed to the holder outer cylinder 105 is mounted inside the specimen holder H2. The support member 106 is provided with cylindrical holes 107a and 107b in which the spherical bodies 103a and 103b can move along the X-axis. The probes 1a and 1b are moved along the X-axis by movement of the spherical bodies 103a and 103b relative to the inner walls of the cylindrical holes 107a and 107b in the spherical body support member 106. At this time, the portions of the inner walls of the cylindrical holes 107a and 107b which make contact with the spherical bodies 103a and 103b act as sliding portions.

Movement of the probe 1a or 1b along the Y- or Z-axis is made by pushing or pulling the –X-direction end of the lever 102a or 102b along the Y- or Z-axis using the micrometer head 14a, 14b, 15a, or 15b. For example, movement of the probe 1a in the Y-direction is made as follows. First, the –X-direction end of the lever 102a is pushed in the –Y-direction by means of the micrometer head 14a. At this time, the probe 1a rotates about the spherical body 103 in the Y-direction. The portion of the spherical body 103a in abutment with the inner wall of the cylindrical hole 107a in the spherical body support member 106 acts as a sliding portion. Since a spring 17a (FIG. 2D) is mounted in a position opposite to the micrometer head 14a to push back the lever, the probe 1a can be rotated in the –Y-direction if the micrometer head is manipulated in the direction to pull it. Manipulations of the micrometer head 14b and manipulations of the micrometer heads 15a, 15b for moving the probes 1a and 1b along the Z-axis are performed on the same principle as the aforementioned manipulation of the micrometer head 14a and so their description is omitted.

That is, the probe position fine adjustment mechanism of the specimen holder H2 is made up of the levers 102a, 102b, spherical bodies 103a, 103b, fixed pins 104a, 104b, spherical body support member 106, micrometer heads 13a, 13b, 14a, 14b, 15a, 15b, and springs 16a, 16b, 17a, 17b, 18a, 18b (see FIGS. 2A, 2C, and 2D).

Embodiment 3

Figure 4A:
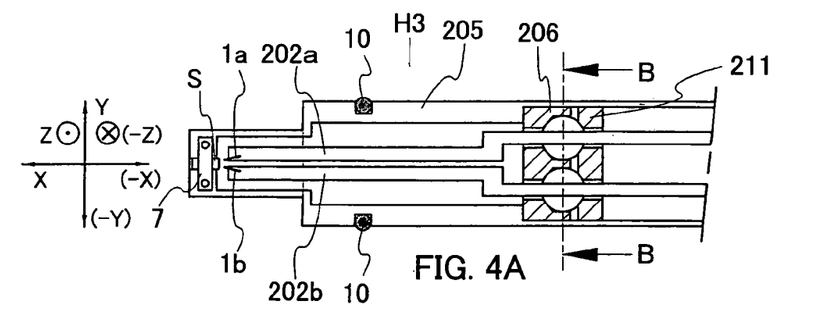
FIGS. 4A and 4B show a further example of pivotal structure for moving a probe for current measurement in three dimensions.
Figure 4B:
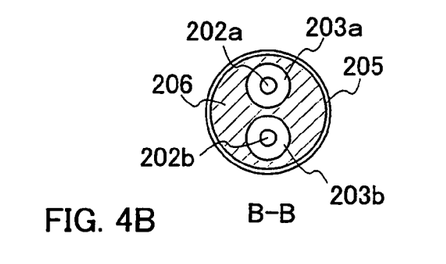

A further example of the structure of the pivotal point for moving the probes 1a and 1b in three dimensions is next described by referring to FIGS. 4A-4B. FIG. 4A is a plan view of a specimen holder H3 as viewed from a side of an electron gun 301. The right half (on the negative side of the X-axis) of the specimen holder H3 is identical in structure and function with the specimen holder H1 of FIG. 2A and so is not shown. FIG. 4B is a cross-sectional view taken on line B-B of FIG. 4A. The electrical wires 9a and 9b connected with the probes 1a and 1b are not shown such that the figures can be read more easily.

Each of the spherical bodies 203a and 203b is provided with a hole extending through it along the X-axis. Levers 202a and 202b are fitted in the through-holes in the spherical bodies 203a and 203b so as to be movable along the X-axis. A spherical body support member 206 is fixed to the holder outer cylinder 205 and has abutment portions in abutment with the spherical bodies 203a and 203b, respectively. The abutment portions have conical seats, respectively. A spherical body-pushing member 211 is pushed in the X-direction by a resilient body (not shown) such that the spherical bodies 203a and 203b make intimate contact with the conical seats of the spherical body support member 206. Motion of the probes 1a and 1b in the X-direction is produced by motion of the levers 202a and 202b relative to the inner walls of the through-holes in the spherical bodies 203a and 203b. At this time, the portions of the levers 202a and 202b which make contact with the inner walls of the through-holes in the spherical bodies 203a and 203b act as sliding portions.

The probes 1a and 1b are moved along the Y- or Z-axis by pushing or pulling the −X-direction ends of the levers 202a and 202b along the Y- or Z-axis by means of the micrometer head 14a, 14b, 15a, or 15b. For example, the probe 1a is moved in the Y-direction as follows. First, the −X-direction end of the lever 202a is pushed in the −Y-direction by the micrometer head 14a. At this time, the probe 1a rotates in the Y-direction about the spherical body 203a. The portions of the conical seat of the spherical body support member 206 and spherical body-pushing member 211 which abut against the spherical body 203a act as sliding portions. Since a spring 17a is mounted in a position opposite to the micrometer head 14a to push back the lever, the probe 1a can be rotated in the −Y-direction if the micrometer head is manipulated in the direction to pull it. Manipulations of the micrometer head 14b and manipulations of the micrometer heads 15a, 15b for moving the probes 1a and 1b along the Z-axis are performed on the same principle as the aforementioned manipulation of the micrometer head 14a and so their description is omitted (see FIGS. 2A, 2C, and 2D).

That is, the probe position fine adjustment mechanism of the specimen holder H3 is made up of the levers 202a, 202b, spherical bodies 203a, 203b, spherical body support member 206, spherical body-pushing member 211, micrometer heads 13a, 13b, 14a, 14b, 15a, 15b, and springs 16a, 16b, 17a, 17b, 18a, 18b.

Embodiment 4

Figure 5A:
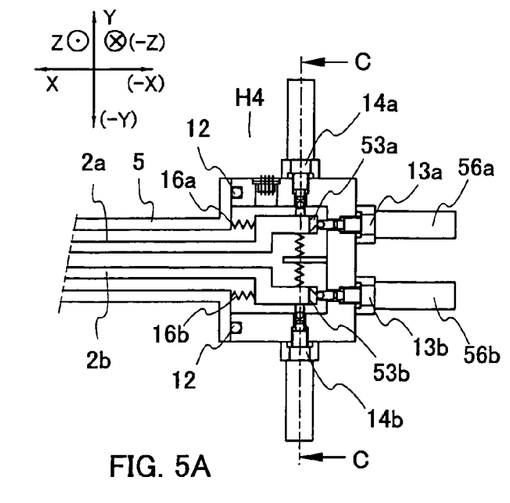
FIGS. 5A and 5B show a lever-moving mechanism for moving a probe for current measurement in three dimensions, the lever-moving mechanism having piezoelectric devices and motors incorporated therein.
Figure 5B:
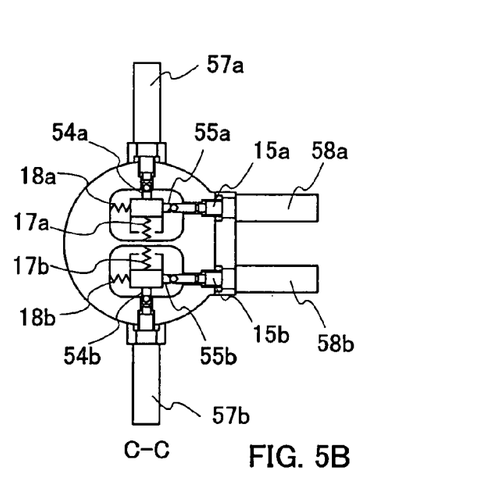

An embodiment of the present invention in which at least one kind of devices of piezoelectric devices and motors is incorporated in a probe position fine adjustment mechanism is next described by referring to FIGS. 5A and 5B.

FIG. 5A is a plan view of the right half of a specimen holder H4 as viewed from a side of the electron gun 301 (on the negative side of the X-axis). In the holder, piezoelectric devices 53a, 53b, 54a, 54b, 55a, and 55b are disposed between micrometer heads 13a, 13b, 14a, 14b, 15a, 15b and levers 2a, 2b. The specimen holder also includes motors 56a, 56b, 57a, 57b, 58a, and 58b for driving the micrometer heads 13a, 13b, 14a, 14b, 15a, and 15b. FIG. 5B is a cross-sectional view taken on line C-C of FIG. 5A. Electrical wires (not shown) for driving the piezoelectric devices and motors are connected with them.

The piezoelectric device 53a mounted between the micrometer head 13a and the lever 2a expands and contracts along the X-axis according to the applied voltage. Where the probe 1a is moved in the X-direction, the applied voltage is adjusted to permit the piezoelectric device 53a to expand. Conversely, if the applied voltage is adjusted such that the piezoelectric device 53a shrinks, the spring 16a located in the corresponding position pushes back the lever, moving the probe 1a in the −X-direction. The piezoelectric devices mounted between the other micrometer heads and levers operate similarly and so their description is omitted. The operation for moving the probe by elongation and contraction of the piezoelectric device is similar to the operation for moving the probe 1a along the X-axis by pushing or pulling the micrometer head 13a. However, where a piezoelectric device is used, the probe can be controlled more finely than where control is provided using a micrometer head. A desired measurement site can be selected while observing a higher resolution image.

Although the micrometer head (such as 13a) shown on the specimen holder H1 of FIGS. 2A to 2D can be directly manually operated by the operator, there are some problems in practical applications. For example, if the micrometer head is touched directly by a hand, mechanical vibrations will be transmitted to the high-resolution image being observed. This blurs the clear image. In the case of a large-sized electron microscope, there is another problem that the operator must stretch his hand to the position where the specimen holder is mounted. This severely deteriorates the manipulability. Furthermore, in some cases, remote control function is required in addition to automation of the apparatus. These problems can be solved by incorporating motors into micrometer heads. In the example of FIGS. 5A and 5B, motors 56a, 56b, 57a, 57b, 58a, and 58b are incorporated in micrometer heads 13a, 13b, 14a, 14b, 15a, and 15b, respectively. The structure of the left half (on the positive side of the X-axis) of FIG. 5A can be applied to any of the aforementioned specimen holders H1, H2, and H3.

In the example of FIGS. 5A and 5B, piezoelectric devices and motors are incorporated at the same time. It is not always necessary that both kinds of devices be incorporated at the same time. The above-described advantages can be derived if only piezoelectric devices or only motors are incorporated.

Embodiment 5

Figure 7A:
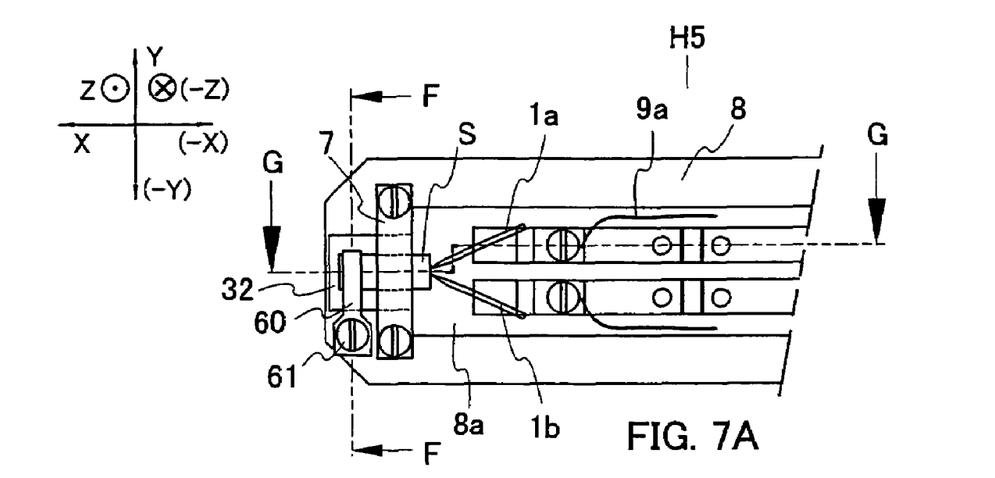
FIGS. 7A-7C show a front-end portion of another specimen holder according to the present invention in enlarged form, the specimen holder having an additional fixed terminal.
Figure 7B:
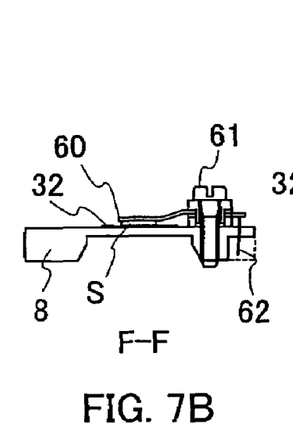
Figure 7C:
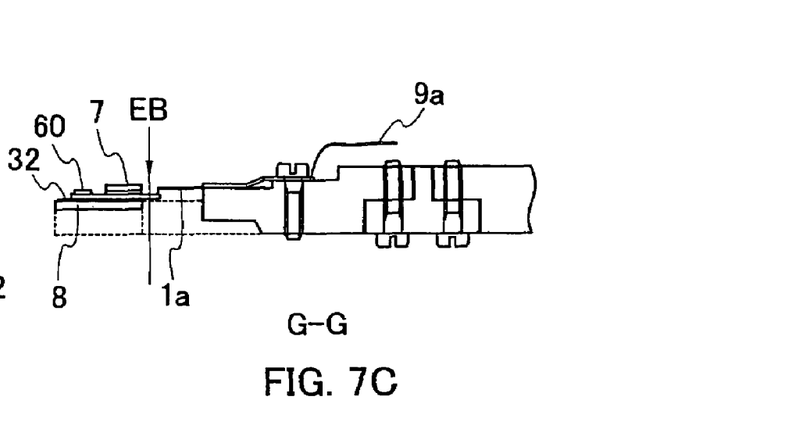

An example in which a fixed terminal is added to the front-end portion of a specimen holder to measure an electrical signal is next described by referring to FIGS. 7A-7C. FIG. 7A is a plan view of the front end of a specimen holder H5 as viewed from the electron gun side. FIGS. 7B and 7C are cross-sectional views taken on lines F-F and G-G, respectively, of FIG. 7A. In the same way as in FIGS. 6B and 6C, the vertical dimension is shown to be exaggerated about twice compared with the actual dimension to facilitate understanding the structure.

In FIGS. 7A to 7C, a specimen S is electrically insulated from a specimen support member 8 and held on the support member 8 by a specimen holding member 7. A leaf spring terminal 60 is fixed to the specimen support member 8 with a screw 61. The screw 61 is electrically insulated from the specimen support member 8 by an insulator (not shown). The leaf spring terminal 60 is electrically connected with the specimen S. An electrical wire 62 is connected with the leaf spring terminal 60 and with an airtight terminal 21. Accordingly, the specimen S can be energized or an electrical signal can be taken from the specimen S via the leaf spring terminal 60. That is, the specimen holder H5 permits a three-terminal measurement using two probes 1a, 1b and the leaf spring terminal 60. The two probes permit selection of measurement sites.

Embodiment 6

Figure 8A:
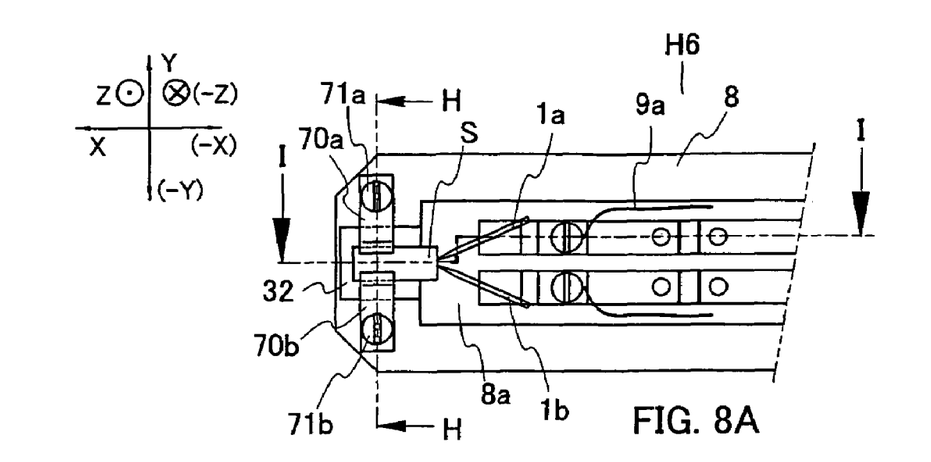
FIGS. 8A-8C show a front-end portion of a further specimen holder according to the present invention in enlarged form, the specimen holder having two additional fixed terminals.
Figure 8B:
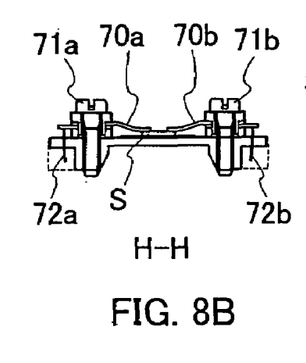
Figure 8C:
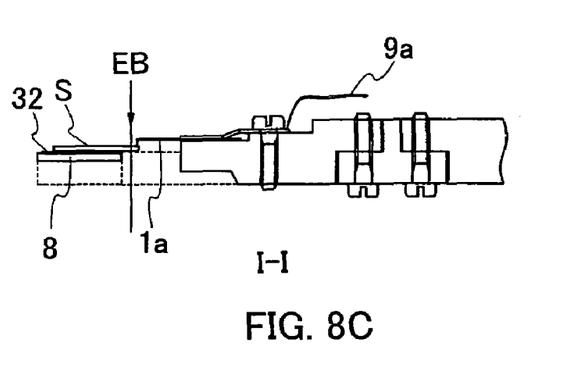

An example in which two fixed terminals for measuring an electrical signal are added to a front-end portion of a specimen holder is next described by referring to FIGS. 8A-8C. FIG. 8A is a plan view of the front end of the specimen holder H6 as viewed from the electron gun side. FIGS. 8B and 8C are cross-sectional views taken on lines H-H and I-I, respectively, of FIG. 8A. In the same way as in FIGS. 6B and 6C, the vertical dimension is shown to be exaggerated about twice compared with the actual dimension to facilitate understanding the structure.

In FIGS. 8A and 8B, a specimen S is held down by leaf spring terminals 70a and 70b at different positions and held on a specimen support member 8. The leaf spring terminals 70a and 70b are fixed by screws 71a and 71b, respectively.

The screws 71a and 71b are electrically insulated from the specimen support member 8 by insulators (not shown). The leaf spring terminals 70a and 70b are electrically connected with the specimen S. Electrical wires 72a and 72b are connected with the leaf spring terminals 70a and 70b, respectively, and with an airtight terminal 21.

Accordingly, the specimen S can be electrically energized or an electrical signal can be taken from the specimen S via the leaf spring terminals 70a and 70b. That is, the specimen holder H6 permits a four-terminal measurement using two probes 1a, 1b and two leaf spring terminals 70a, 70b. The two probes permit selection of measurement sites.

In the above example of specimen holder H5 (FIG. 7A), the specimen holding member 7 and leaf spring terminal 60 are mounted separately. One terminal may act as means for holding down the specimen and also as means performing the function of an electrode. Furthermore, in the example of specimen holder H6, the leaf spring terminals 70a and 70b act to hold the specimen and, at the same time, perform the functions of electrodes. The specimen holding member 7 may be mounted independently of the leaf spring terminals 70a and 70b in the same way as the example of specimen holder H5.

Figure 9A:
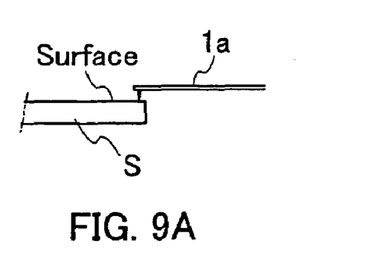
FIGS. 9A and 9B show examples of the shape of the front end of a probe in enlarged form.
Figure 9B:
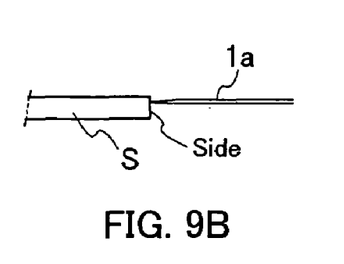

FIGS. 9A and 9B show enlarged side elevations of examples of the front-end shape of the probe 1a making contact with the specimen S. FIG. 9A shows an example of the front-end shape in a case where the surface of the specimen S is examined or measured. For example, a probe as used in a scanning probe microscope can be utilized. FIG. 9B shows an example in which a side of the specimen S is investigated. In the case of this shape, as the front end is made thinner, the distance between two measurement points can be made shorter.

As described so far, according to the present invention, the electrical conductivity between desired two points on a specimen can be measured either during imaging or before and after imaging by the use of at least two probes for current measurement, the probes being capable of being adjusted in position along three axes. Furthermore, if a fixed terminal is added, electrical characteristics of a quite small area can be measured by a four-terminal method using a TEM.

Having thus described our invention with the detail and particularity required by the Patent Laws, what is desired protected by Letters Patent is set forth in the following claims.

The invention claimed is:

1. A specimen holder for an electron microscope having an electron optical column, said specimen holder comprising:
   a specimen holder installation member extending through the electron optical column;
   a specimen holder outer cylinder supported by the specimen holder installation member so as to be movable along an axis of the specimen holder extending through the electron optical column, the axis intersecting an electron beam path;
   a specimen support member supported at a front end of said specimen holder outer cylinder and having an opening through which an electron beam passes;
   specimen holding means for holding said specimen in such a way that the specimen holding means plugs a part of said opening and that the specimen is electrically insulated from said specimen support member; and
   a probe position fine adjustment mechanism for bringing at least one probe for current measurement into desired positions on the specimen, the probe being capable of being adjusted in position along three mutually perpendicular axes including said axis of the specimen holder, wherein said probe fine adjustment mechanism comprises:
   a lever having a front-end portion carrying the probe thereon while electrically isolated from the probe;
   a spherical body which allows movement of the lever along the axis of the holder and which acts as a pivotal point permitting movement of the front end of the probe in two axial directions perpendicular to the axis of the holder by rotation of the lever;
   a support member for supporting the spherical body to the specimen holder outer cylinder;
   a translational motion mechanism disposed at an end of the lever located opposite to the end of the lever carrying the probe with the spherical body interposed therebetween and acting to move the lever in the three axial directions including the direction of the axis of the holder; and
   a resilient body mounted in a position opposite to said translational motion mechanism with the lever interposed therebetween to push back the lever.

2. A specimen holder for an electron microscope having an electron optical column, said specimen holder comprising:
   a specimen holder installation member extending through the electron optical column;
   a specimen holder outer cylinder supported by the specimen holder installation member so as to be movable along an axis of the specimen holder extending through the electron optical column, the axis intersecting an electron beam path;
   a specimen support member supported at a front end of said specimen holder outer cylinder and having an opening through which an electron beam passes;
   specimen holding means for holding said specimen in such a way that the specimen holding means plugs a part of said opening and that the specimen is electrically insulated from said specimen support member; and
   a probe position fine adjustment mechanism for bringing at least two probes for current measurement into desired positions on the specimen, the probes being capable of being adjusted in position along three mutually perpendicular axes including said axis of the specimen holder, wherein
   (A) said probe position fine adjustment mechanism has a spherical body fixed in position in the direction of the axis of the holder, two levers between which said spherical body is interposed, and resilient bodies each located between said holder outer cylinder and a respective one of the levers,
   (B) said levers having abutment portions abutting against said spherical body, each of said abutment portions being provided with a V-groove,
   (C) said spherical body being urged into intimate contact with said V-grooves by said resilient bodies,
   (D) said probes being movable in the direction of the axis of the holder by movement of said levers relative to said spherical body,
   (E) said probes being movable along two axes perpendicular to the direction of the axis of the holder by rotation of the probe about the spherical body, said rotation being produced by a translational motion mechanism at the ends of the levers opposite to the front-end portions of the levers carrying the probe such that the spherical body is interposed between them, and
   (F) during said rotation of said levers, the V-grooves in the levers against which said spherical body abuts act as sliding portions.

3. A specimen holder for an electron microscope having an electron optical column, said specimen holder comprising:
   a specimen holder installation member extending through the electron optical column;

a specimen holder outer cylinder supported by the specimen holder installation member so as to be movable along an axis of the specimen holder extending through the electron optical column, the axis intersecting an electron beam path;

a specimen support member supported at a front end of said specimen holder outer cylinder and having an opening through which an electron beam passes;

specimen holding means for holding said specimen in such a way that the specimen holding means plugs a part of said opening and that the specimen is electrically insulated from said specimen support member; and a probe position fine adjustment mechanism for bringing at least two probes for current measurement into desired positions on the specimen, the probes being capable of being adjusted in position along three mutually perpendicular axes including said axis of the specimen holder, wherein (A) said probe position fine adjustment mechanism has two levers fifed in through-holes in two spherical bodies and a spherical body support member fixed to said holder outer cylinder, the two levers being fixed to prevent their motion relative to the spherical body, (B) said spherical body support member has two cylindrical holes in which said two spherical bodies respectively move in the direction of the axis of the holder, (C) said probes being movable in the direction of the axis of the holder by relative motion between each of said spherical bodies and the inner wall of a respective one of said cylindrical holes, (D)) said probes being movable along two axes perpendicular to the direction of the axis of the holder by rotation of the probe about the spherical bodies, said rotation being produced by a translational motion mechanism at the ends of the levers opposite to the front-end portions of the levers carrying the probe such that the spherical bodies are interposed between them, and (E) during said rotation of said levers, portions of said spherical body support member against which said spherical bodies abut act as sliding portions.

4. A specimen holder for an electron microscope having an electron optical column, said specimen holder comprising:

a specimen holder installation member extending through the electron optical column;

a specimen holder outer cylinder supported by the specimen holder installation member so as to be movable along an axis of the holder extending through the electron optical column, the axis intersecting an electron beam path;

a specimen support member supported to a front end of said specimen holder outer cylinder and having an opening through which an electron beam passes;

specimen holding means for holding said specimen in such a way that the specimen holding means plugs a part of said opening and that the specimen is electrically insulated from said specimen support member; and a probe position fine adjustment mechanism for bringing at least two probes for current measurement into desired positions on the specimen, the probes being capable of being adjusted in position alone three mutually perpendicular axes including said axis of the holder, wherein (A) said probe position fine adjustment mechanism has two spherical bodies each provided with a through-hole extending in the direction of the axis of the holder, two levers fitted in said through-holes and capable of moving relative to said spherical bodies in the direction of the axis of the holder, a spherical body support member fixed to said holder outer cylinder, and a spherical body-pushing member for pushing said spherical bodies against said spherical body support member, (B) said spherical body support member has abutment portions which abut against the spherical bodies, each of said abutment portions having a conical seat, said spherical body-pushing member acting to push the spherical bodies into intimate contact with the conical seats of the spherical body support member, (C) said probes being movable in the direction of the axis of the holder by moving the levers relative to the through-holes in the spherical bodies, (D) said probes being movable along two axes perpendicular to the direction of the axis of the holder by rotation of the probe about the spherical bodies, said rotation being produced by a translational motion mechanism at the ends of the levers opposite to the ends of the levers carrying the probe with the spherical bodies interposed between the ends, said translational motion being made along two axes perpendicular to the direction of the axis of the holder, and (E) during said rotation, said conical seats of the spherical body support member abutting against said spherical bodies and said spherical body-pushing member act as sliding portions.

5. A specimen holder for an electron microscope as set forth in claim 1, 2, 3, or 4, wherein said probe position fine adjustment mechanism has piezoelectric devices each of which is mounted between said translational motion mechanism and a respective one of said levers.

6. A specimen holder for an electron microscope as set forth in claim 1, 2, 3, or 4, wherein said probe position fine adjustment mechanism has a built-in motor for driving said translational motion mechanism.

7. A specimen holder for an electron microscope as set forth in claim 1, 2, 3, or 4, wherein there is further provided an electrode which is electrically insulated from said specimen support member and mounted to said specimen support member, said electrode having a terminal making contact with said specimen.

8. A specimen holder for an electron microscope as set forth in claim 1, 2, 3, or 4, wherein there are further provided at least two specimen holding members which make contact with the specimen at different positions to hold said specimen to said specimen support member and which can be used as electrodes electrically insulated from said specimen support member.

\* \* \* \* \*

UNITED STATES PATENT AND TRADEMARK OFFICE
CERTIFICATE OF CORRECTION

| | | |
|---|---|---|
| PATENT NO. | : 7,566,884 B2 | Page 1 of 1 |
| APPLICATION NO. | : 11/440695 | |
| DATED | : July 28, 2009 | |
| INVENTOR(S) | : Deguchi et al. | |

It is certified that error appears in the above-identified patent and that said Letters Patent is hereby corrected as shown below:

Column 13, Line 20, "levers fifed in" should read -- levers fitted in --

Column 14, Line 2, "alone three" should read -- along three --

Signed and Sealed this

Seventeenth Day of November, 2009

David J. Kappos
*Director of the United States Patent and Trademark Office*